United States Patent [19]

Goto et al.

[11] Patent Number: 4,973,693

[45] Date of Patent: Nov. 27, 1990

[54] PENTACYCLIC COMPOUND AND STEREOSELECTIVE SYNTHESIS THEREOF

[76] Inventors: Shunsuke Goto, Fujisawa Pharmaceutical Co., Ltd. 1-6, Kashima 2-chome Yodogawa-ku, Osaka 532, Japan; Tohru Fukuyama, Department of Chemistry Rice University, Houston, Tex. 77251-1892

[21] Appl. No.: 401,746

[22] Filed: Sep. 1, 1989

[51] Int. Cl.⁵ .......................................... C07D 498/08
[52] U.S. Cl. .......................................... 544/63; 544/73
[58] Field of Search .................................... 544/63, 73

[56] References Cited

U.S. PATENT DOCUMENTS 4,645,765  2/1987  Kohsaka et al. ................. 544/73

OTHER PUBLICATIONS

Shimamura et al., J. Antibiotics, 40, 1987, pp. 600–606.
Kiyoto et al., J. Antibiotics, 40, 1987, pp. 594–599.
Iwami et al., J. Antibiotics, 40, 1987, 589–593.
Uchida et al., JACS., 109, 1987, pp. 4108–4109.

Primary Examiner—Mukund J. Shah
Assistant Examiner—E. C. Ward
Attorney, Agent, or Firm—Oblon, Spivak, McClelland, Maier & Neustadt

[57] ABSTRACT

Novel pentacyclic compounds having antimicrobial and antitumor activity and a process for preparing the same. The pentacyclic compounds are also useful as intermediates in the production of known tetracyclic antitumor compounds.

15 Claims, 4 Drawing Sheets

PENTACYCLIC COMPOUND AND STEREOSELECTIVE SYNTHESIS THEREOF

BACKGROUND OF THE INVENTION

1. Field of the Invention

The present invention is related to the synthesis of a novel pentacyclic compound. The pentacyclic compound is a useful intermediate in the synthesis of known tetracyclic antitumor compounds.

2. Discussion of the Background

Tetracyclic compounds having the general structure shown below

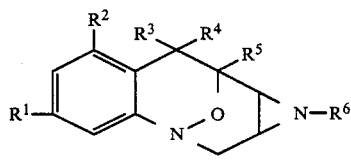

and pharmaceutical salts thereof are known to have antitumor activity, antimicrobial activity, etc. and are useful for the treatment of tumors and infectious diseases in mammals. Such compounds, their synthesis and their use in treating infectious diseases and tumors are disclosed, for example, in U.S. Pat. No. 4,645,765 and U.S. application Ser. No. 06/947,759, filed Dec. 30, 1986.

The compound known as FR-No. 900482 shown below

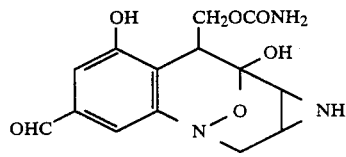

has been isolated from a culture broth of *Streptomyces sandaensis* and has been shown to exhibit potent antitumor activities. See (a) Iwami, M. et al; J. Antibiot., 1987, 40:589. (b) Kiyoto, S. et al; ibid. 1987, 40:594. (c) Shimomura, K. et al; ibid, 1987, 40:600. (d) Uchida, I. et al; J. Am. Chem. Soc., 1987, 109:4108. Biological testing against experimental tumors has shown that FR-No. 900482 has a similar activity to mitomycin C and is active against mytomycin C and vincristine-resistant P388 cells. Like mytomycin C, FR-No. 900482 is thought to be activated in the cells to form interstrand DNA-DNA cross-links (Masuda, K.; Nakamura, T.; Shimomura, K.; Shibata, T.; Terano, H.; Kohsaka, M., J. Antibiot., 1988, 41:1497). The organic synthesis of compounds such as FR-No. 900482 presents a formidable challenge to synthetic chemists due to the large number of asymmetric carbons and the presence of a labile hydroxyl amine moiety.

There continues to be a need for a new more efficient synthesis of potent antitumor and antimicrobial agents having intricate chemical structures in general. More specifically, a need exists for a new synthetic method for preparing antitumor agents having the general structure shown above.

SUMMARY OF THE INVENTION

Accordingly, one object of the present invention is to provide a synthetic method for preparing suitable intermediates useful in the synthesis of antitumor agents having the general structure I shown above.

A further object of the invention is to provide novel intermediate compounds which are not only useful as intermediates in the synthesis of known antitumor compounds, but also may be useful as antitumor and antimicrobial agents themselves.

Still another object of the invention is to provide new antitumor agents.

These and other objects which will become apparent from the following specification have been achieved by the present invention which is directed to a novel process for the production of pentacyclic intermediate compounds and new antitumor agents.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawing, wherein.

DETAILED DESCRIPTION OF THE PREFERRED EMBODIMENTS

Figure 1A:
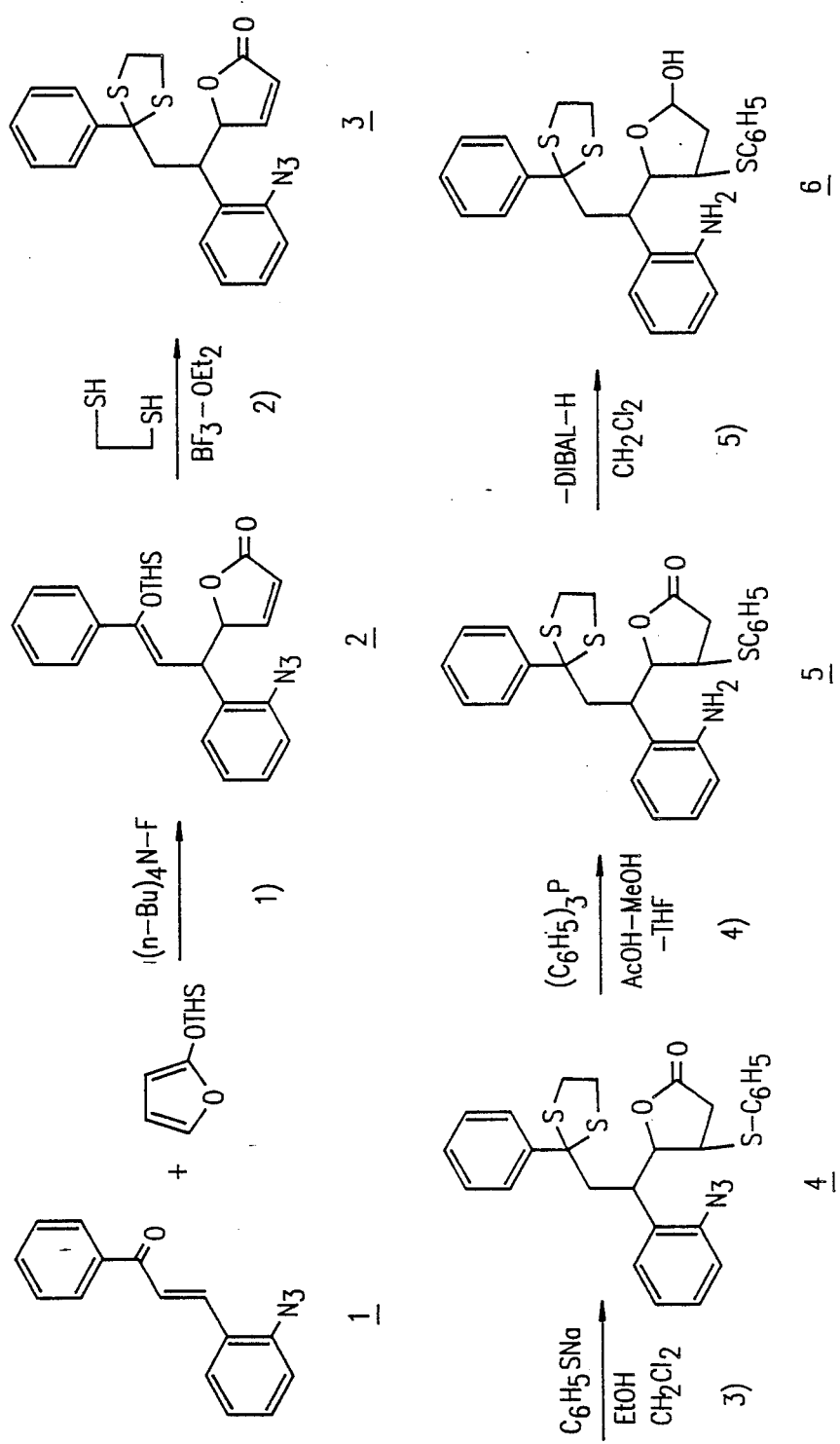
FIG. 1 shows a preferred synthetic sequence for preparation of the pentacyclic compounds of the present invention.

The process of the present invention provides an efficient synthesis of a pentacyclic compound which possesses all the necessary synthetic functionality to further prepare known antimicrobial and antitumor compounds.

Known antimicrobial and antitumor compounds are disclosed in U.S. Pat. No. 4,645,765 and in U.S. application Ser. No. 06/947,759, filed Dec. 30, 1986. The specifications of these references are incorporated herein by reference to provide a more complete description of the known antitumor and antimicrobial compounds, their method of use and methods for their preparation.

These known compounds and pharmaceutically acceptable salts thereof are particularly useful in the treatment of tumors such as carcinoma (e.g., squamous cell carcinoma, transitional cell carcinoma, adenocarcinoma, cystoadenocarcinoma, etc.) and sarcoma, for example, connective tissue tumors (e.g., fibrosarcoma, etc.), neurogenic tumors (e.g., melanoma, etc.), hematopoietic tissue tumors (e.g., malignant lymphoma, lymphatic leukemia, reticulosis, etc.) in all organs and tissues, and similar tumors in mammals including human beings.

These compounds are also useful as antimicrobial agents against various pathogenic microorganisms, for example, *Bacillus subtilis, Escherichia coli* and *Pseudomonas aeruginosa*. The antimicrobial use of these compounds is, of course, not limited to these specific microorganisms.

In one aspect, the present invention is directed to novel pentacyclic compound having the structure shown below and pharmaceutically acceptable salts thereof.

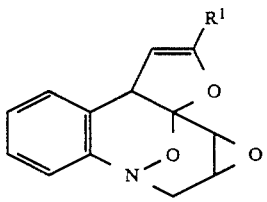

In this structure, the group R¹ represents an unsubstituted or substituted aromatic group. The aromatic group may be a carbocyclic aromatic group such as a phenyl or naphthyl group or derivatives thereof, or the aromatic group may be an aromatic heterocyclic group such as a furanyl, thiophenyl, nicotinyl, isonicotinyl, thiazolyl, thiadiazolyl, tetrazolyl, imidazolyl, etc. and derivatives thereof. Both the carbocyclic and heterocyclic aromatic groups may be substituted with one or more suitable substituents such as lower alkyl (e.g., methyl, ethyl, propyl, isopropyl, butyl, pentyl, hexyl, etc.), halogen (e.g., chlorine, bromine, iodine, fluorine), lower alkoxy (e.g., methoxy, ethoxy, propoxy, isopropoxy, butoxy, pentyloxy, hexyloxy, etc.), nitro, lower alkylthio (e.g., methylthio, ethylthio, propylthio, isopropylthio, butylthio, pentylthio, hexylthio, etc.) groups and the like.

Preferred aromatic groups "R¹" are carbocyclic aromatic groups, wherein unsubstituted carbocyclic aromatic groups are most preferred. A particularly preferred aromatic group is phenyl.

With respect to the compounds (I) and (II) of this invention, it is to be understood that there may be one or more stereoisomeric pairs such as optical and geometrical isomers due to the asymmetric carbon atoms, and such isomers are also included within a scope of this invention.

Suitable salts of the object compounds (I) are conventional pharmaceutically acceptable salts and may include a salt with a base such as an inorganic base salt, for example, an alkali metal salt (e.g., sodium salt, potassium salt, etc.), an alkaline earth metal salt (e.g., calcium salt, magnesium salt, etc.), an ammonium salt, an organic base salt, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); a salt with an acid such as an inorganic acid addition salt (e.g., hydrochloride, hydrobromide, sulfate, phosphate, etc.), an organic acid addition salt (e.g., formate, acetate, trifluoroacetate, maleate, tartrate, methanesulfonate, benzenesulfonate, toluenesulfonate, etc.); a salt with a basic or acidic amino acid (e.g., arginine, aspartic acid, glutamic acid, etc.); and the like.

Another aspect of the present invention provides pharmaceutical compositions which contain the tricyclo compounds of the present invention.

The pharmaceutical composition of this invention can be used in the form of a pharmaceutical preparation, for example, in solid, semisolid or liquid form, which contains the tricyclo compounds (I), as active ingredients, in admixture with an organic or inorganic carrier or excipient suitable for external, enteral or parenteral applications. The active ingredients may be compounded, for example, with conventional non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. Compound (I) is included in the pharmaceutical composition in an amount sufficient to produce the desired effect upon the process or condition of diseases.

For applying this composition to humans, it is preferable to apply it by parenteral or enteral administration. While the dosage of therapeutically effective amount of the tricyclo compounds (I) varies from and also depends upon the age and condition of each individual patient to be treated, a daily dose of about 0.1–1000 mg, preferably 0.5–500 mg and more preferably 1–100 mg, of the active ingredients is generally given for treating diseases, and an average single dose of about 1 mg, 5 mg, 10 mg, 50 mg, 100 mg, 250 mg and 500 mg is generally administered.

Figure 1B:
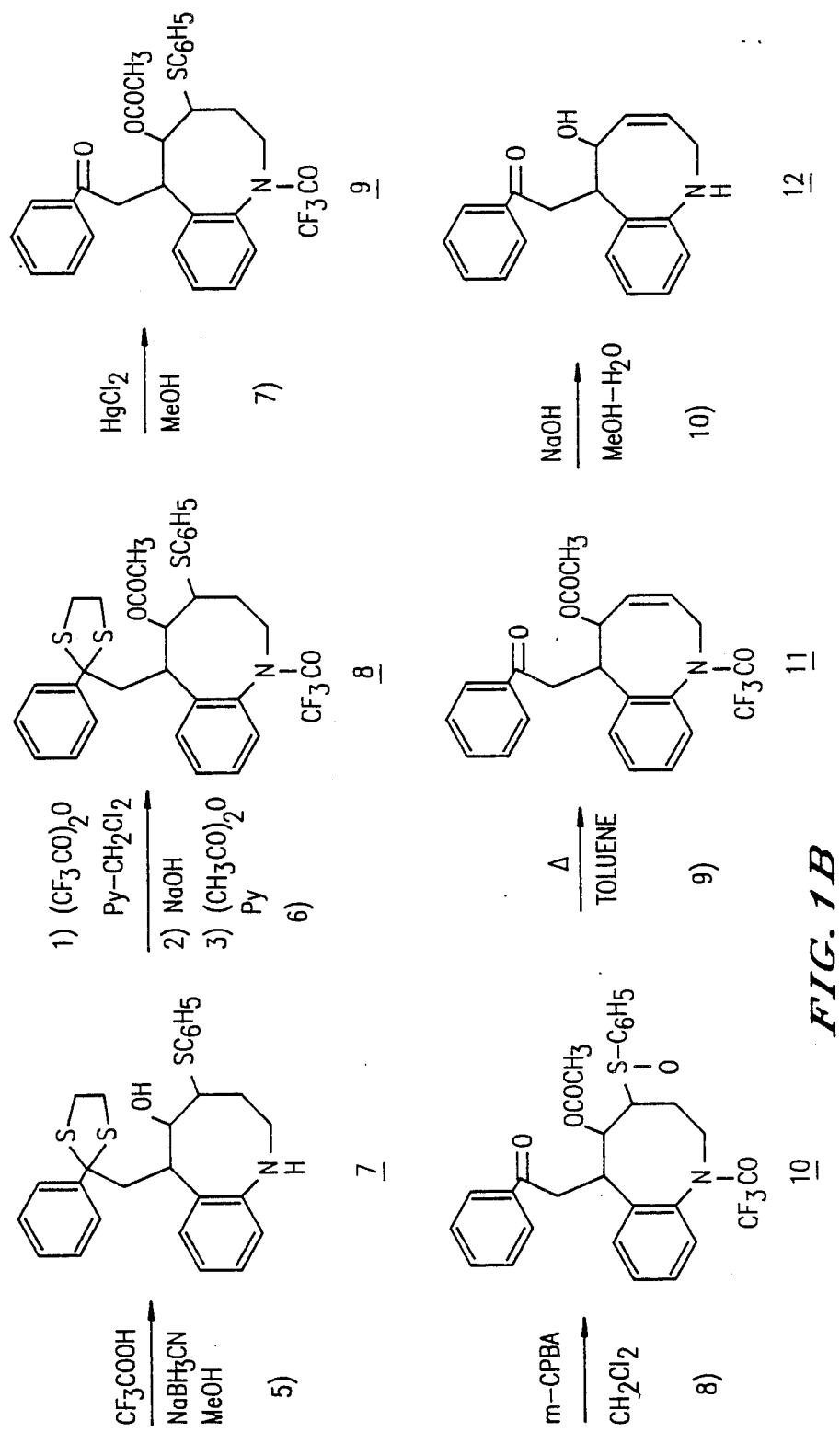
Figure 1C:
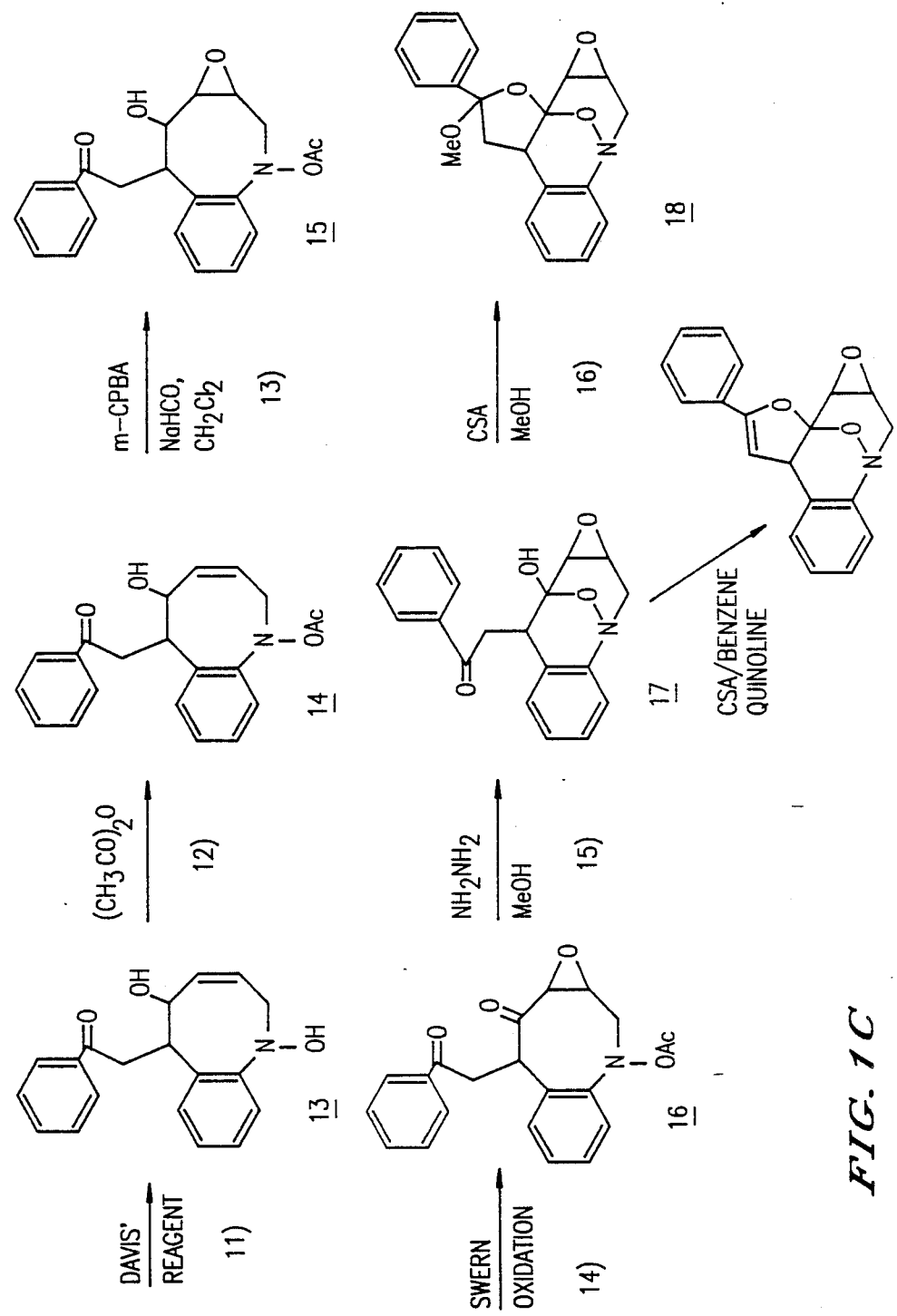
Figure 1D:
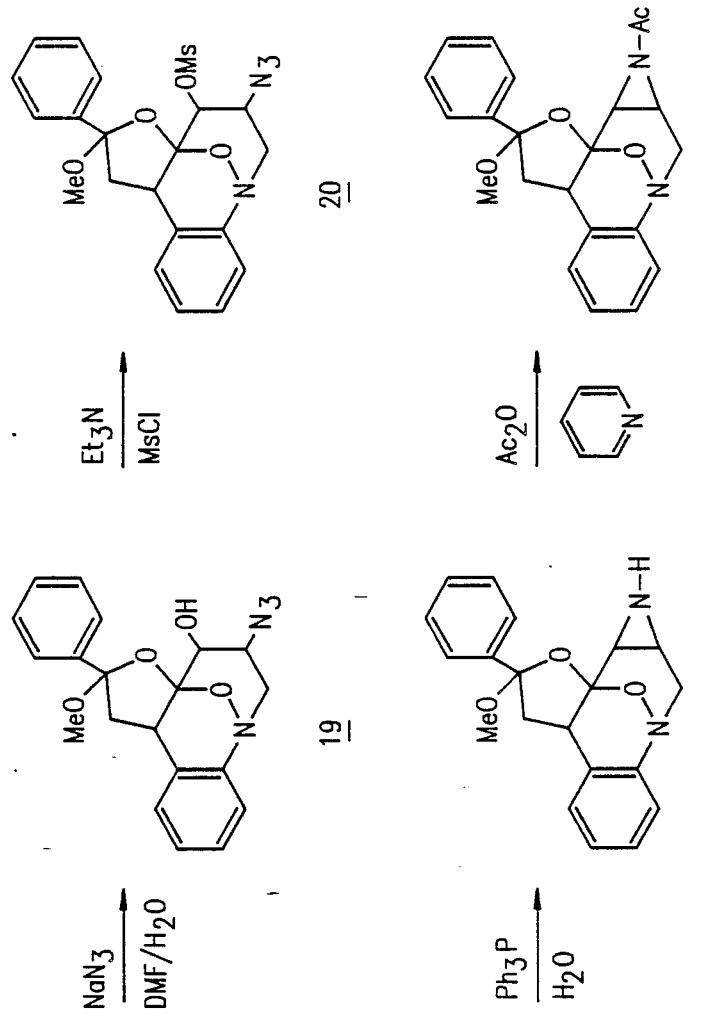

The novel pentacyclic compounds of the present invention may be prepared from readily available starting materials. For clarity, the synthetic procedure of the present invention will be illustrated using phenyl as the aromatic group. However, it is to be understood that other aromatic species such as those described above may be used in the process of the present invention so long as the aromatic species is sufficiently stable to the reaction conditions and may be carried through the reaction scheme. Appropriate starting materials for the preparation of pentacyclic compounds in which the aromatic group is other than phenyl can be readily prepared by known synthetic chemistry to provide suitable starting materials. For example, the use and preparation of substituted phenyl groups or heterocyclic aromatic groups in compounds analogous to compound 1 (see FIG. 1) will be readily apparent to one skilled in the art.

In the method of the present invention, 2-trimethylsiloxyfuran is added to an appropriate chalcone (1) to give the desired adduct (2) as shown in FIG. 1. The starting chalcone can be prepared from readily available 2-aminobenzyl alcohol by a three-step reaction sequence as follows: (1) $HNO_2/NaN_3$, (2) PCC, (3) PhCOMe, NaOH. Chalcone derivatives used to prepare pentacyclic compounds in which the aromatic group is other than phenyl can be prepared by derivatizing the 2-aminobenzyl alcohol or utilizing a suitable heterocyclic alcohol.

The labile silyl enol ether adduct (2) is then converted to the thioketal (3) and the highly reactive butenolide is protected to prevent further reaction. A preferred protecting group is obtained by adding thiophenol to give sulfide (4). Additional protecting groups which may be added across the carbon-carbon double bond of the butenolide and which function to prevent further reaction of the butenolide are considered to be within the scope of the present invention.

Once the butenolide has been protected, the protected compound can be cleanly reduced to give an amine, such as compound 5. Partial reduction of the lactone in compound 5 to a lactol (6) followed by intramolecular reductive amination gives an 8-membered amine (7). The amino and hydroxy groups in compound 7 are then protected using suitable amino-protecting and hydroxy-protecting groups such as for example the trifluoroacetamide and acetate groups shown in compound 8. Other amino-protecting and hydroxy-protecting groups which may be removed under alkaline conditions may also be used in the present invention.

The conversion of the amino lactol (6) to an 8-membered amine by intramolecular reductive amination is a surprising and essential step in the synthesis. The formation of medium size rings is difficult and has conventionally presented a challenge to synthetic chemists. As compared with 5- and 6-membered rings, 8-membered rings are disfavored both entropically and enthalpically. The present process provides a means of forming an 8-membered cyclic amine ring system and further elaboration of this ring system to form the pentacyclic intermediate and ultimately the pentacyclic aziridine compounds of the present invention.

Deprotection of the thioketal (8) gives a ketone (9). The remaining sulfide group is then converted to an olefin (11) by thermolysis of the corresponding sulfoxide (10). The sulfoxide can be prepared by oxidation of the phenyl sulfide using an appropriate oxidizing agent such as for example metachloroperbenzoic acid (MCPBA). Alkaline hydrolysis of the olefin (11) gives an amino alcohol (12).

The nitrogen atom in the amino alcohol is then oxidized to give the corresponding hydroxyl amine (13). A preferred oxidizing agent is Davis' reagent (Davis, F. A.; Billmers, J. M.; Gosciniak, D. J.; Towson, J. C.; Bach, R. D., J. Org. Chem., 1986, 51:4240, and references cited therein and Zajac, W. W., Jr.; Walters, T. R.; Darcy, M. G., J. Org. Chem., 1988, 53:5856). Other oxidizing agents which produce the desired hydroxyl amine and which do not degradatively oxidize the amino alcohol compound may also be used.

The hydroxyl amine is unstable and is immediately protected using an appropriate protecting group such as a lower acyl group (e.g., acetyl, propionyl, butyryl, isobutyryl, valeryl, isovaleryl, pivalyl, hexanoyl, etc.). Preferably, the hydroxylamine is protected as an acetate (see FIG. 1, compound 14).

The allyl alcohol moiety in the protected hydroxylamine is then oxidized, preferably with MCPBA, to give an epoxide (15). Oxidation of the remaining hydroxyl group followed by hydrazinolysis gives a tautomeric mixture of hemiketals (17). The hemiketals are then subjected to dehydrative cyclization to give the desired compound having formula I or may be cyclized to form the alkoxy compound 18 if alcohol solvent is used.

Suitable "imino-protecting group", "amino-protecting group" and the hydroxy-protecting groups as discussed herein include aralkyl such as (lower)-alkyl (e.g. benzyl, phenethyl, phenylpropyl, phenylbutyl, phenylpentyl, phenylhexyl, naphthylmethyl, naphthylpropyl, benzhydryl, trityl, etc.), acyl such as carbamoyl, aliphatic acyl, aromatic acyl, heterocyclic acyl and aliphatic acyl substituted with aromatic or heterocyclic group(s) derived from carboxylic, carbonic, sulfonic and carbamic acids.

The novel pentacyclic compounds of the present invention may be used to synthesize tetracyclic antitumor and antimicrobial agents by conversion of the epoxide to an aziridine.

The epoxide (18) can be converted to the aziridine, for example, by opening the epoxide ring using an azide such as sodium azide (Compound 19) followed by conversion of the resulting hydroxyl group to a good leaving group such as the tosyl or mesyl group, for example as in the mesyl azide (20). Reduction of the azide with triphenyl phosphine, for example, yields the desired aziridine 21 which may be acylated, if desired, to give acetate (22). Obviously, any suitable leaving group other than mesyl or tosyl may be utilized in the formation of the aziridine.

The aziridine compounds have the general formula shown below.

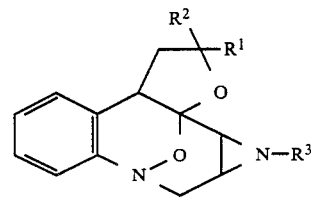

In this formula, $R^1$ is an unsubstituted or substituted aromatic group and is the same as $R^1$ in formula I described above. $R^2$ is a lower alkoxy group having 1–6 carbon atoms, such as methoxy, ethoxy, n-propoxy, isopropoxy, n-butyloxy, etc. In a preferred embodiment, $R^2$ is methoxy. $R^3$ is hydrogen or an iminoprotecting group such as defined above. A particularly preferred imino-protecting group is acetyl.

The novel aziridine compounds having formula II exhibit antitumor activity, antimicrobial activity, etc. and are also useful for the treatment of tumors and infectious diseases in mammals.

Other features of the invention will become apparent in the course of the following descriptions of exemplary embodiments which are given for illustration of the invention and are not intended to be limiting thereof.

EXAMPLES

In the examples, the following abbreviations are used.

| | |
|---|---|
| THF: tetrahydrofuran | MeOH: methanol |
| NaCl: sodium chloride | $CH_2Cl_2$: dichloromethane |
| $NaHCO_3$: sodium hydrogen carbonate | DMSO: dimethyl sulfoxide |
| NaOH: sodium hydroxide | $H_2O$: water |
| HCl: hydrochloric acid | DMF: dimethylformamide |
| $Na_2SO_3$: sodium sulfite | $NaN_3$: sodium azide |
| TLC: thin layer chromatography (silica gel) | |

EXAMPLE 1 - PREPARATION OF COMPOUND 2

To a solution of compound 1 (1.5 g) in THF (15 ml) was added 2-trimethylsiloxyfuran (1.6 ml) at room temperature. After cooling to −78° C., a solution of tetra-n-butylammonium fluoride in THF (1.6M; 0.06 ml) was added to the reaction mixture. After stirring for ten minutes, the reaction mixture was poured into a mixture of saturated aqueous NaCl and $NaHCO_3$ solution. Extraction of the mixture with ether and evaporation of the extract afforded 2 (2.63 g) as a yellow oil.

NMR ($CDCl_3$, δ): 0.02 (9H, s), 4.58 (1H, dd, J=9.5 Hz, 4.4 Hz), 5.3 (2H, m), 6.07 (1H, dd, J=4.4 Hz, 2.1 Hz), 7.0–7.5 (10H, m).

EXAMPLE 2 - PREPARATION OF COMPOUND 3

To a solution of compound 2 (2.63 g) in ethanedithiol (10 ml) and dichloroethane (15 ml) was added boron trifluoride etherate (1.5 ml) at room temperature. After stirring at room temperature for 5 hours, the reaction mixture was diluted with ether and washed successively with 3N—NaOH, water and saturated NaCl solution. The organic layer was concentrated under vacuum and the residue was purified with silica gel chromatography (eluent: 60% ether in hexane) to give 3 (2.09 g) as a yellow oil.

NMR (CDCl$_3$, δ): 2.8–3.5 (6H, m), 5.07 (1H, br d, J=5.4 Hz), 6.05 (1H, dd, J=5.4 Hz, 2.0 Hz) 6.8–7.7 (10H, m).

EXAMPLE 3 - PREPARATION OF COMPOUND 4

To a solution of compound 3 (2.09 g) in ethanol (15 ml) and dichloromethane (8 ml) was added an alcoholic solution of sodium thiophenoxide (prepared from 1.13 g of thiophenol and 0.29 g of sodium hydride) with stirring at 0° C. After stirring for 30 minutes, fifteen drops of acetic acid were added to the reaction mixture. Partition with ether and saturated NaCl solution, and separation with silica gel chromatography (eluent: 60% ether in hexane) gave 4 (2.15 g) as a yellow oil.

NMR (CDCl$_3$, δ): 2.38 (1H, dd, J=18.2 Hz, 3.3 Hz), 2.6–3.5 (9H, m), 4.2–4.6 (1H, br), 6.6–7.6 (14H, m).

EXAMPLE 4 - PREPARATION OF COMPOUND 5

To a solution of compound 4 (3.25 g) in THF (32.5 ml), methanol (65 ml) and acetic acid (13 ml) was added triphenylphosphine (1.95 g) at room temperature. After stirring for 1 hour, the reaction mixture was concentrated under vacuum. The residue was dissolved in dichloromethane and washed with saturated NaHCO$_3$ solution. The organic layer was concentrated under vacuum to give a crystalline residue, which was triturated with methanol to give 5 (2.82 g) as a white crystal.

NMR (CDCl$_3$, δ): 2.32 (1H, dd, J=18.5 Hz, 3.3 Hz), 2.5–3.8 (9H, m), 4.34 (1H, br d, J=7.7 Hz), 6.5–6.9 (3H, m), 6.9–7.3 (9H, m), 7.4–7.8 (2H, m).

EXAMPLE 5 - PREPARATION OF COMPOUNDS 6 AND 7

To a solution of compound 5 (1.74 g) in dichloromethane (70 ml) was added a toluene solution of diisobutylaluminum hydride (1.5M; 4.7 ml) at −78° C. After stirring at the same temperature for 30 minutes, the reaction mixture was poured into a saturated aqueous NaCl solution. After the aluminum hydroxide was filtered off, the dichloromethane layer was concentrated to give 6 as a yellow oil. To a solution of 6 in methanol (35 ml) and dichloromethane (14 ml) were added trifluoroacetic acid (270 μl) and sodium cyanoborohydride (0.22 g) at room temperature. After stirring for 15 minutes the reaction mixture was poured into a saturated aqueous NaCl—NaHCO$_3$ solution and extracted with dichloromethane. After evaporation of the solvent, the residual oil was purified by silica gel chromatography (eluent: 80% ether in hexane) to give 7 as a white amorphous powder (1.30 g).

NMR (CDCl$_3$, δ): 2.6–3.8 (13H, m), 6.7–7.3 (12H, m), 7.4–7.7 (2H, m).

EXAMPLE 6 - PREPARATION OF COMPOUND 8

To a solution of compound 7 (500 mg) in dichloromethane (30 ml) and pyridine (0.17 ml) was added trifluoroacetic anhydride (0.27 ml) dropwise at 0° C. After 30 minutes, the reaction mixture was washed with saturated aqueous NaHCO$_3$ solution and concentrated to give a yellow oil. The yellow oil was dissolved in methanol (15 ml) and treated with a small amount of 15% NaOH solution (25 μl) for 30 minutes at 0° C. The resulting methanolic solution was concentrated under vacuum. The residue was dissolved in pyridine (5 ml) and acetic anhydride (2.5 ml) and stirred overnight. The reaction mixture was concentrated under vacuum. After dissolving the residue in dichloromethane, the solution was washed with 1N—HCl solution, saturated aqueous NaHCO$_3$ solution and NaCl solution. The organic layer was concentrated to give 8 (627 mg) as a yellow oil.

NMR (CDCl$_3$, δ): 2.21 (3H, s), 2.4–3.6 (11H, m), 4.28 (1H, br d, J=14.1 Hz), 5.01 (1H, dd, J=10.3 Hz, 1.8 Hz), 6.8–7.8 (14H, m).

EXAMPLE 7 - PREPARATION OF COMPOUND 9

To a solution of compound 8 (627 mg) in methanol (60 ml) was added mercuric chloride (1.26 g) at room temperature. While the suspension was refluxed for 5 hours, the additional portion of mercuric chloride (1.6 g) was added twice at every 2 hours. The reaction mixture was filtered with celite. After the evaporation of the methanolic solution, the residue was extracted with dichloromethane and saturated aqueous NaCl solution. The organic layer was concentrated under vacuum to give 9 (547 mg) as a yellow oil.

NMR (CDCl$_3$, δ): 2.2 (3H, s), 2.4–3.8 (7H, m), 4.3 (1H, br d, J=14 Hz), 5.0 (1H, dd, J=10.0 Hz, 2 Hz), 6.8–7.8 (14H,m).

EXAMPLE 8 - PREPARATION OF COMPOUND 10

To a solution of compound 9 (339 mg) in dichloromethane (15 ml) was added a solution of m-chloroperbenzoic acid (157.4 mg) in dichloromethane (5 ml) at 0° C. After stirring for 10 minutes, the reaction mixture was washed with saturated aqueous Na$_2$SO$_3$ and NaHCO$_3$ solution. The organic layer was concentrated under vacuum and separated with TLC (developing solvent: 5% MeOH in CH$_2$Cl$_2$) to give 10 (265 mg) as a yellow oil.

EXAMPLE 9 - PREPARATION OF COMPOUND 11

A solution of compound 10 (264 mg) in toluene (5 ml) was heated at 175° C. in a sealed tube for 6 hours. The reaction mixture was diluted with ether and washed with saturated aqueous NaHCO$_3$ solution. After the evaporation of the solvent, the residual oil was purified with TLC (developing solvent: 3% MeOH in CH$_2$Cl$_2$) to give 11 (182.3 mg) as a yellow oil.

NMR (CDCl$_3$, δ): 2.25 (3H, s), 3.0–4.5 (5H, m), 5.0–6.0 (3H, m), 6.6–7.7 (8H, m), 7.8–8.0 (1H, m).

EXAMPLE 10 - PREPARATION OF COMPOUND 12

To a solution of compound 11 (252 mg) in methanol (25 ml) was added 15% aqueous NaOH solution (2.5 ml) at room temperature. The mixture was refluxed for 20 minutes and cooled to room temperature. After concentration under vacuum, the residue was extracted with dichloromethane. The evaporation of the solvent and TLC (developing solvent: 3% MeOH in CH$_2$Cl$_2$) separation afforded 12 (124 mg) as a yellow oil.

NMR (CDCl$_3$, δ): 3.2–4.0 (5H, m), 5.0–5.5 (2H, m), 5.5–6.0 (1H, m), 6.6–7.7 (8H, m), 7.8–8.0 (1H, m).

EXAMPLE 11 - PREPARATION OF COMPOUND 13

To a solution of compound 12 (186 mg) in THF (18 ml) was added Davis' reagent (498 mg) at room temperature. After stirring overnight, the reaction mixture was concentrated under vacuum. Separation with TLC (developing solvent: 3% MeOH in CH$_2$Cl$_2$) gave 13 (176 mg) as a colorless crystal.

NMR (CDCl$_3$, δ): 3.2–3.9 (5H, m), 4.12 (1H, br d, J=14.1 Hz), 4.6–5.0 (1H, br s), 5.0–5.7 (3H, m), 6.8–7.7 (8H, m), 7.7–8.0 (3H, m).

EXAMPLE 12 - PREPARATION OF COMPOUND 14

Compound 13 (175 mg) was suspended in acetic anhydride (5 ml) at room temperature. While the suspension was stirred for 1 hour at room temperature, it became a clear solution. The reaction mixture was concentrated under vacuum, and separated with TLC (developing solvent: 3% MeOH in CH$_2$Cl$_2$) to give 14 (188 mg) as a yellow oil.

NMR (CDCl$_3$, δ): 2.1 (3H, s), 3.2–3.9 (5H, m), 3.9–4.4 (2H, m), 4.9–6.0 (4H, m), 7.0–7.7 (7H, m), 7.7–8.1 (2H, m).

EXAMPLE 13 - PREPARATION OF COMPOUND 15

To a solution of compound 14 (417 mg) in dichloromethane (21 ml) were added NaHCO$_3$ (1.0 g) and a dichloromethane solution of m-chloroperbenzoic acid (1.28 g in 10 ml) at room temperature. After stirring overnight, the reaction mixture was washed with saturated aqueous Na$_2$SO$_3$ and NaHCO$_3$ solution. The organic layer was concentrated under vacuum and separated with TLC (developing solvent: 3% MeOH in CH$_2$Cl$_2$) to give 15 (341 mg) as a yellow oil.

NMR (CDCl$_3$, δ): 2.09 (3H, s), 2.70 (1H, dd, J=9.8 Hz, 4.6 Hz) 2.92 (1H, dd, J=8.5 Hz, 4.6 Hz), 3.1–4.0 (5H, m), 4.2–4.7 (1H, t, J=8.5 Hz), 7.0–7.7 (8H, m), 7.8–8.1 (2H, m).

EXAMPLE 14 - PREPARATION OF COMPOUND 16

To a solution of DMSO (0.66 ml) in dichloromethane (30 ml) was added oxalyl chloride (0.41 ml) at −78° C. After 3 minutes, a dichloromethane solution of compound 15 (341 mg) was added to the reaction mixture which was stirred for more 15 minutes at the same temperature. To the reaction mixture was added triethylamine (2.59 ml) to stop the oxidation and then washed with saturated aqueous NaHCO$_3$-NaCl solution. Evaporation of the solvent and separation with TLC (developing solvent: 3% MeOH in CH$_2$Cl$_2$) afforded 16 (267 mg) as a colorless oil.

NMR (CDCl$_3$, δ): 2.00 (3H, s), 2.9–3.2 (2H, m), 3.2–3.8 (4H, m), 4.3–4.8 (2H, m), 7.2–7.6 (7H, m), 7.9–8.2 (2H, m).

EXAMPLE 15 - PREPARATION OF COMPOUND 17

To a solution of compound 16 (266 mg) in methanol (15 ml) was added hydrazine (0.133 ml) at 0° C. After stirring for 1 hour, the reaction mixture was diluted with dichloromethane and washed with saturated aqueous NaCl solution. The organic layer was concentrated under vacuum and separated with TLC (developing solvent: 80% ether in hexane) to afford 17 (208.6 mg) as a colorless oil.

NMR (CDCl$_3$, δ): 2.6–3.1 (2H, m), 3.1—4.1 (6H, m), 6.7–7.7 (7H, m), 7.8–8.1 (2H, m).

EXAMPLE 16 - PREPARATION OF COMPOUND 18

To a solution of compound 17 (40.0 mg) in methanol (4 ml) was added d-camphorsulfonic acid (20 mg) at room temperature. After stirring for 2 hours, the reaction mixture was extracted with dichloromethane and saturated aqueous NaHCO$_3$ solution. The organic layer was concentrated under vacuum and separated with TLC (developing solvent: 80% ether in hexane) to give 18 (31.8 mg) as a colorless oil.

NMR (CDCl$_3$, δ): 2.23 (1H, d, J=11.3 Hz), 2.82 (1H, dd, J=11.3 Hz, 6.7 Hz), 3.29 (3H, s), 3.3–3.6 (3H, m) 3.78 (1H, dd, J=14.1 Hz, 7.2 Hz), 4.15 (1H, br d, J=14.1 Hz), 6.7–7.7 (9H, m).

EXAMPLE 17 - PREPARATION OF COMPOUNDS 19 and 20

To a solution of compound 18 (31.8 mg) in DMF (3.2 ml) and H$_2$O (0.32 ml) was added NaN$_3$ (62 mg). The reaction mixture was heated to 120° C. and stirred for 6 hours. The mixture was poured into a saturated aqueous NaCl solution. The mixture was extracted with dichloromethane and the extract was concentrated to afford 19 as a yellow oil. To a solution of 19 in dichloromethane (3 ml) was added triethylamine (90 μl) and mesyl chloride (30 μl) at 0° C. After stirring for 15 minutes, the reaction mixture was washed with saturated aqueous NaHCO$_3$ solution and concentrated under vacuum. Purification with TLC (developing solvent: 3% MeOH in CH$_2$Cl$_2$) gave 20 (29 mg) as a colorless oil.

NMR (CDCl$_3$, δ): 2.25 (1H, d, J=12.3 Hz), 2.92 (1H, dd, J=12.3 Hz, 7.7 Hz), 3.22 (3H, s), 3.25 (3H, s), 3.51 (1H, m), 3.78 (1H, dd, J=12.6 Hz, 7.5 Hz), 4.13 (1H, d, J=12.6 Hz), 4.0–4.4 (1H, m), 4.91 (1H, d, J=2.0 Hz), 6.9–7.6 (9H, m).

EXAMPLE 18 - PREPARATION OF COMPOUND 21

To a solution of compound 20 (5 mg) in THF (5 ml) and water (50 μl) was added triphenylphosphine (10 mg). The reaction mixture was heated to 60° C. for 1 hour and concentrated under vacuum. Separation with (developing solvent: 3% MeOH in CH$_2$Cl$_2$) gave 21 (3.5 mg) as a colorless oil.

NMR (CDCl$_3$, δ): 2.17 (1H, d, J=12.1 Hz), 2.44 (1H, dd, J=9.0 Hz, 2.3 Hz), 2.78 (1H, dd, J=12.1 Hz, 6.9 Hz), 3.13 (1H, d, J=6.9 Hz), 3.30 (3H, s), 3.53 (1H, d, J=4.4 Hz), 3.70 (1H, s), 3.90 (1H, dd, J=14.1 Hz, 4.4 Hz), 4.05 (1H, dd, J=14.1 Hz, 2.3 Hz), 6.6–7.8 (9H, m).

EXAMPLE 19 - PREPARATION OF COMPOUND 22

To a solution of compound 21 (3.5 mg) in pyridine (1 ml) was added acetic anhydride (0.5 ml) and stirred for 1.5 hours at room temperature. Evaporation of the mixture and purification with TLC (developing solvent 3% in CH$_2$Cl$_2$) gave 22 as a colorless oil (4 mg).

NMR (CDCl$_3$, δ): 2.01 (3H, s), 2.17 (1H, d, J=11.8 Hz), 2.83, (1H, dd, J=11.8 Hz, 7.7 Hz), 2.90 (1H, dd, J=6.9 Hz, 2.6 Hz), 3.32 (3H, s), 3.47 (1H, d, J=3.8 Hz), 3.55 (1H, d, J=7.7 Hz), 3.77 (1H, s), 3.82 (1H, dd, J=12.8 Hz, 6.9 Hz), 4.07 (1H, dd, J=12.8 Hz, 2.6 Hz), 6.6–7.7 (9H, m).

Obviously, numerous modifications and variations of the present invention are possible in light of the above teachings. Accordingly, it is to be understood that the present invention may be practiced otherwise than as specifically described herein.

What is claimed as new and desired to be secured by Letters Patent of the United States is:

1. A pentacyclic compound having formula I shown below

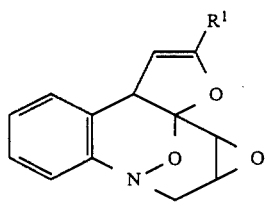

wherein $R^1$ is an unsubstituted carbocyclic or heterocyclic aromatic group or a carbocyclic or heterocyclic aromatic group substituted with at least one lower alkyl, lower alkoxy, halogen, lower alkylthio or nitro group, and pharmaceutically acceptable salts thereof.

2. The compound of claim 1, wherein $R^1$ is a carbocyclic aromatic or substituted carbocyclic aromatic group.

3. The compound of claim 2, wherein said aromatic group is phenyl.

4. The compound of claim 2, wherein $R^1$ is an unsubstituted heterocyclic aromatic group or a heterocyclic aromatic group substituted with at least one lower alkyl, lower alkoxy, halogen, lower alkylthio or nitro groups.

5. The compound of claim 4, wherein $R^1$ is selected from the group consisting of furanyl, thiophenyl, nicotinyl, isonicotinyl, thiazolyl, thiadiazolyl, tetrazolyl, and imidazolyl groups.

6. The compound of claim 1, wherein said compound is

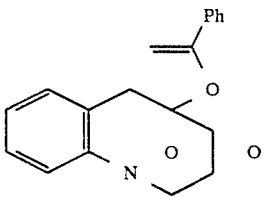

7. A pentacyclic aziridine compound having formula II shown below

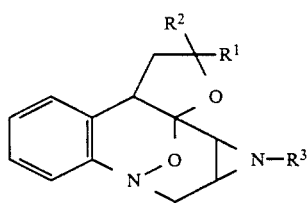

wherein $R^1$ is an unsubstituted carbocyclic or heterocyclic aromatic group or a carbocyclic or heterocyclic aromatic group substituted with at least one lower alkyl, lower alkoxy, halogen, lower alkylthio or nitro group, $R^2$ is a $C_{1-6}$ lower alkoxy group and $R^3$ is hydrogen or an imino-protecting group.

8. The aziridine of claim 7, wherein $R^1$ is a carbocyclic aromatic or substituted carbocyclic aromatic group.

9. The aziridine compound of claim 8, wherein said aromatic group is phenyl.

10. The aziridine compound of claim 7, wherein $R^1$ is an unsubstituted heterocyclic aromatic group or a heterocyclic aromatic group substituted with at least one lower alkyl, lower alkoxy, halogen, lower alkylthio or nitro groups.

11. The aziridine compound of claim 10, wherein $R^1$ is selected from the group consisting of furanyl, thiophenyl, nicotinyl, isonicotinyl, thiazolyl, thiadiazolyl, tetrazolyl, and imidazolyl.

12. The aziridine compound of claim 7, wherein $R^2$ is methoxy.

13. The aziridine compound of claim 7, wherein $R^3$ is acetyl.

14. A pentacyclic compound having formula I shown below

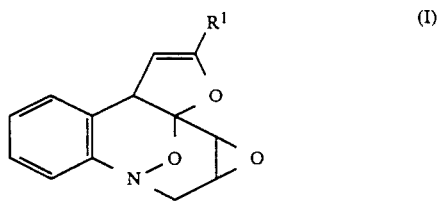

wherein $R^1$ an unsubstituted carbocyclic or heterocyclic aromatic group selected from the group consisting of phenyl, naphthyl, furanyl, thiophenyl, nicotinyl, isonicotinyl, thiazolyl, thiadiazolyl, tetrazolyl and imidazolyl or said carbocyclic or heterocyclic aromatic group substituted with at least one lower alkyl, lower alkoxy, halogen, lower alkylthio or nitro group, and pharmaceutically acceptable salts thereof.

15. A pentycyclic aziridine compound having formula II shown below

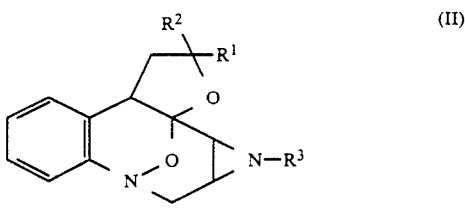

wherein $R^1$ is an unsubstituted carbocyclic or heterocyclic aromatic group selected from the group consisting of phenyl, naphthyl, furanyl, thiophenyl, nicotinyl, isonicotinyl, thiazolyl, thiadiazolyl, tetrazolyl and imidazolyl or said carbocyclic or heterocyclic aromatic group substituted with at least one lower alkyl, lower alkoxy, halogen, lower alkylthio or nitro group, $R^2$ is a $C_{1-6}$ lower alkoxy group and $R^3$ is hydrogen or an imino-protecting group.

* * * * *